US012520954B2

(12) United States Patent
Polley

(10) Patent No.: US 12,520,954 B2
(45) Date of Patent: Jan. 13, 2026

(54) SAFETY BED FOR CHILDREN AND ADULTS

(71) Applicant: SENSORY MEDICAL INC., Denver, CO (US)

(72) Inventor: Caleb Polley, Denver, CO (US)

(73) Assignee: Sensory Medical Inc., Denver, CO (US)

( * ) Notice: Subject to any disclaimer, the term of this patent is extended or adjusted under 35 U.S.C. 154(b) by 205 days.

(21) Appl. No.: 18/265,638

(22) PCT Filed: Dec. 7, 2021

(86) PCT No.: PCT/US2021/062245
§ 371 (c)(1),
(2) Date: Jun. 6, 2023

(87) PCT Pub. No.: WO2022/125573
PCT Pub. Date: Jun. 16, 2022

(65) Prior Publication Data

US 2024/0041678 A1 Feb. 8, 2024

Related U.S. Application Data

(60) Provisional application No. 63/122,220, filed on Dec. 7, 2020.

(51) Int. Cl.
*A47D 9/00* (2006.01)
*A47C 17/86* (2006.01)
(Continued)

(52) U.S. Cl.
CPC .............. *A47D 9/012* (2022.08); *A47C 17/86* (2013.01); *A47D 7/02* (2013.01); *A47D 9/00* (2013.01);
(Continued)

(58) Field of Classification Search
CPC . A47D 9/012; A47D 9/00; A47D 7/02; A47D 15/008; A47C 17/86; A47C 21/08;
(Continued)

(56) References Cited

U.S. PATENT DOCUMENTS 4,641,387 A * 2/1987 Bondy ................ A61G 7/0526 5/512
5,081,722 A * 1/1992 Yu .......................... A47D 9/008 5/915
(Continued)

FOREIGN PATENT DOCUMENTS

AU 2016225053 A1 10/2017
CA 3200971 A1 * 6/2022 ............ A47C 17/86
(Continued)

OTHER PUBLICATIONS

International Patent Application No. PCT/US2021/062245, Search Report and Written Opinion dated Mar. 15, 2022, 8 pages.
(Continued)

*Primary Examiner* — Robert G Santos
(74) *Attorney, Agent, or Firm* — Charles B. Lobsenz; Potomac Law Group, PLLC

(57) ABSTRACT

A safety bed for children and adults who may have special needs includes a frame having a base frame, an upper frame and four vertical poles between the base frame and the upper frame at their respective corners; a mattress support structure supported by the base frame; and an enclosure attached to the frame, said enclosure comprising a ceiling, a base and four walls. A mattress within the enclosure is supported by the mattress support structure so that a sheet may be attached to the four walls of the enclosure at a position approximately equal to the top of the mattress. The enclosure may include a variety of device for monitoring and communicating with an occupant of the bed, including a camera, a light source
(Continued)

and other sensors that may be remotely controlled over a network.

17 Claims, 10 Drawing Sheets

(51) Int. Cl.
*A47D 7/02* (2006.01)
*A61B 5/00* (2006.01)
*A61B 5/11* (2006.01)
*A61G 7/05* (2006.01)
*A61H 23/02* (2006.01)
*A61L 9/04* (2006.01)

(52) U.S. Cl.
CPC .......... *A61B 5/1115* (2013.01); *A61B 5/6891* (2013.01); *A61G 7/0526* (2013.01); *A61H 23/02* (2013.01); *A61L 9/04* (2013.01); *A61G 7/05* (2013.01)

(58) Field of Classification Search
CPC ....... A47C 29/00; A47C 29/003; A47C 31/00; A61B 5/1115; A61B 5/6891; A61G 7/0526; A61G 7/05; A61G 10/005; A61H 23/02; A61L 9/04
USPC .............................. 5/97, 93.1, 424, 425, 427
See application file for complete search history.

(56) References Cited

U.S. PATENT DOCUMENTS 5,384,925 A * 1/1995 Vail ........................ A61G 7/053 5/310
5,566,407 A * 10/1996 Lien ..................... A47C 21/046 5/663
6,175,981 B1 * 1/2001 Lizama .................. A47D 9/057 5/915
6,487,735 B1 12/2002 Jacques, II et al.
6,694,547 B1 * 2/2004 Vail ...................... A47C 29/003 5/424
6,897,781 B2 * 5/2005 Cooper .............. G08B 21/0446 340/517
7,430,770 B2 * 10/2008 Ramirez .............. A61G 7/0526 5/97
7,827,631 B2 * 11/2010 Holman ................. A47D 9/012 5/100
8,413,269 B1 4/2013 Vail
9,629,475 B2 * 4/2017 Veron .................... G08B 25/08
10,188,222 B2 * 1/2019 Veron ................ G08B 21/0205
2003/0066132 A1 * 4/2003 Jacques, II ............. A47C 21/08 5/424
2004/0107984 A1 6/2004 Kline
2004/0189475 A1 9/2004 Cooper et al.
2005/0235418 A1 * 10/2005 Jacques ................ A61G 7/0514 5/424
2006/0168722 A1 * 8/2006 Ramirez .............. A61G 7/0526 5/98.1
2009/0070929 A1 * 3/2009 Holman ................... A47D 7/03 5/93.1
2015/0302721 A1 * 10/2015 Schmidt ............... G01G 19/445 5/93.1
2016/0183695 A1 * 6/2016 Veron ................ G08B 21/0205 5/93.1
2017/0224129 A1 * 8/2017 Veron .................... A47D 15/00
2019/0183254 A1 6/2019 Blackett
2019/0342942 A1 11/2019 Deros et al.
2024/0041678 A1 * 2/2024 Polley ...................... A47D 9/00

FOREIGN PATENT DOCUMENTS

JP 2018512191 A 5/2018
WO WO-2022125573 A1 * 6/2022 ............. A47C 17/86

OTHER PUBLICATIONS

"Boogaloo Beds", Indataproject, Apr. 15, 2019 (Apr. 15, 2019), Retrieved from the Internet URL:https://www.youtube.com/watch?v=4SgSMpIWOf0 on Jan. 27, 2022, 4 pages.
Hagen, M "Boogaloo Beds—Better Sleep. Better Life . A Smart Sleep System For People With Special Needs", Closing the Gap, Nov. 27, 2019 (Nov. 27, 2019), Retrieved from the Internet <URL:https://www.closingthegap.com/boogaloo-beds-better-sleep-better-life-a-smart-sleep-system-for-people-with-special-needs/> on Aug. 9, 2022, 8 pages.
European Search Opinion in corresponding European Patent Application No. 21904268.6, 3 pages.
Japanese Office Action in corresponding Japanese Patent Application No. 2023-558663 mailed Apr. 30, 2025, 8 pages with English Machine Translation by Google.

* cited by examiner

Zipper Safety Pocket from inside

SAFETY BED FOR CHILDREN AND ADULTS

CROSS REFERENCE TO RELATED APPLICATIONS

This application claims priority to Provisional Patent Application U.S. Ser. No. 63/122,220 filed Dec. 7, 2020 and incorporated herein by reference.

FIELD

The present invention relates to safety accessories and more particularly to a bed with features for ensuring safe and comfortable sleep for children and adults with special needs.

BACKGROUND

Poor sleep affects behavior, energy, learning and growth. Children and adults with special needs may benefit from environments where stimuli may be carefully controlled to create optimum conditions for falling and staying asleep for a variety of reasons. In some cases, children and adults with special needs may be likely to leave their bed during unsupervised periods, especially when caregivers are sleeping. Further, they may suffer seizures or other unsafe behavior, such as self-injury or an inability to control themselves. Some children and adults with special needs may create unsafe situations in normal beds by burrowing between a mattress and headboard or under bed coverings in such a way as to cause injury, entrapment or suffocation.

SUMMARY OF THE EMBODIMENTS

A safety bed for children and adults with special needs provides a safe, enclosed environment with mechanisms for controlling stimuli that facilitate restful sleep.

In a first aspect, a safety bed includes a frame having base frame, an upper frame and four vertical poles between the base frame and the upper frame at their respective corners; a mattress support structure supported by the base frame; and an enclosure attached to the frame, said enclosure comprising a ceiling, a base and four walls.

In a further aspect, the safety bed includes a mattress within the enclosure and supported by the mattress support structure. Further, a sheet may be attached to the four walls of the enclosure at a position approximately equal to the top of the mattress.

In another aspect, the enclosure may include an electronics hub, said electronics hub including a camera, a light source and other sensors that may be remotely controlled over a network.

DETAILED DESCRIPTION OF THE EMBODIMENTS

Figure 1:
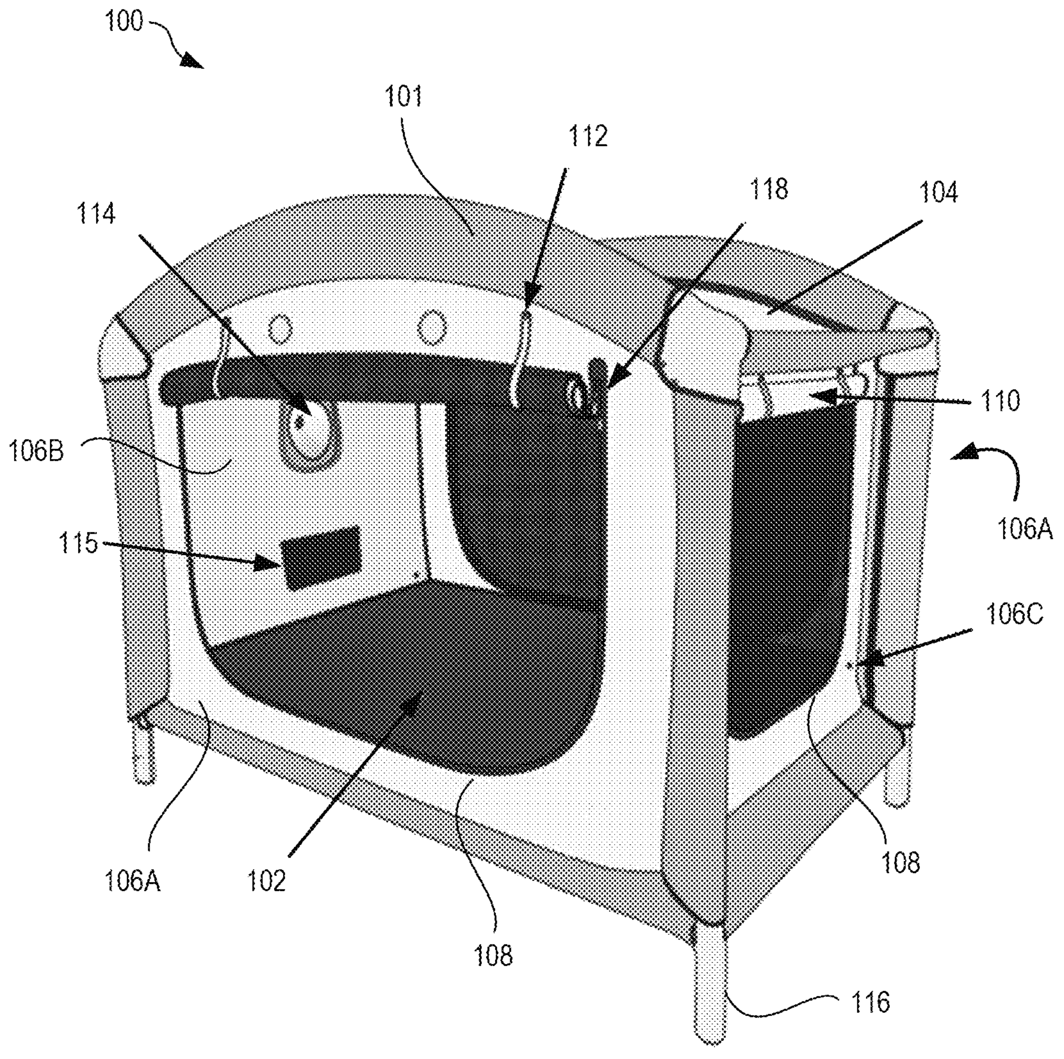
FIG. 1 depicts a safety bed, in embodiments.

FIG. 1 shows a safety bed 100 for children and adults with special needs, in embodiments. Bed 100 is generally rectangular, and includes a base 102, a ceiling 104 and four walls 106* where "*" may represent A, B, C or D. Walls 106* include two side walls 106A, a head wall 106B and an end wall 106C. Together, base 102, ceiling 104 and walls 106* form enclosure 101 supported by a frame 116, described in more detail below. A mattress (not shown) may be placed on base 102. Side walls 106A and end wall 106C may include an opening 108. A door, or flap 110 may be used to close opening 108 by means of zippers 118. In embodiments, flap 110 may include two layers, one of mesh and one of fabric so that opening 108 may be closed with a mesh flap for greater air flow, or a solid fabric flap to reduce light and stimulation. When not in use, flaps 110 may be rolled up and retained by straps 112, which may be attached to wall 106 in a removable way.

Head wall 106B may include an electronics hub 114. Several devices may be included in electronics hub 114, including a light, a camera, a speaker, a microphone or various sensors, for example. Electronics hub 114 may be connected to a power source. Electronics hub 114 may also be connected to a communications network such as a Wi-fi, Bluetooth or cellular network so that devices included in electronics hub 114 may be controlled or monitored remotely from bed 100 by a mobile device or any computing device capable of connected to a communications network. Head wall 106B may also include other features, such as a pocket 115.

Figure 2:
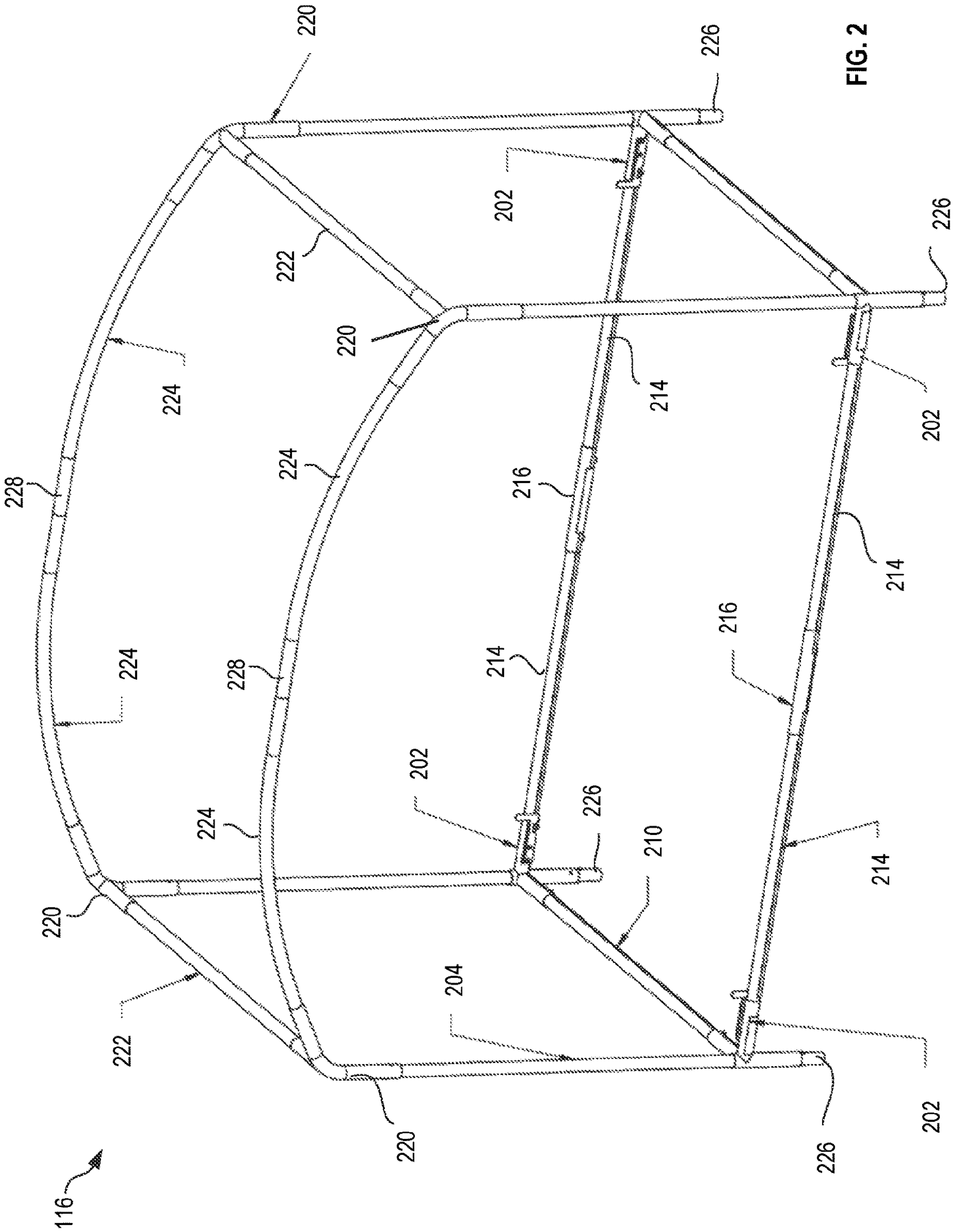
FIG. 2 depicts a frame for use with the safety bed of FIG. 1, in embodiments.
Figure 3:
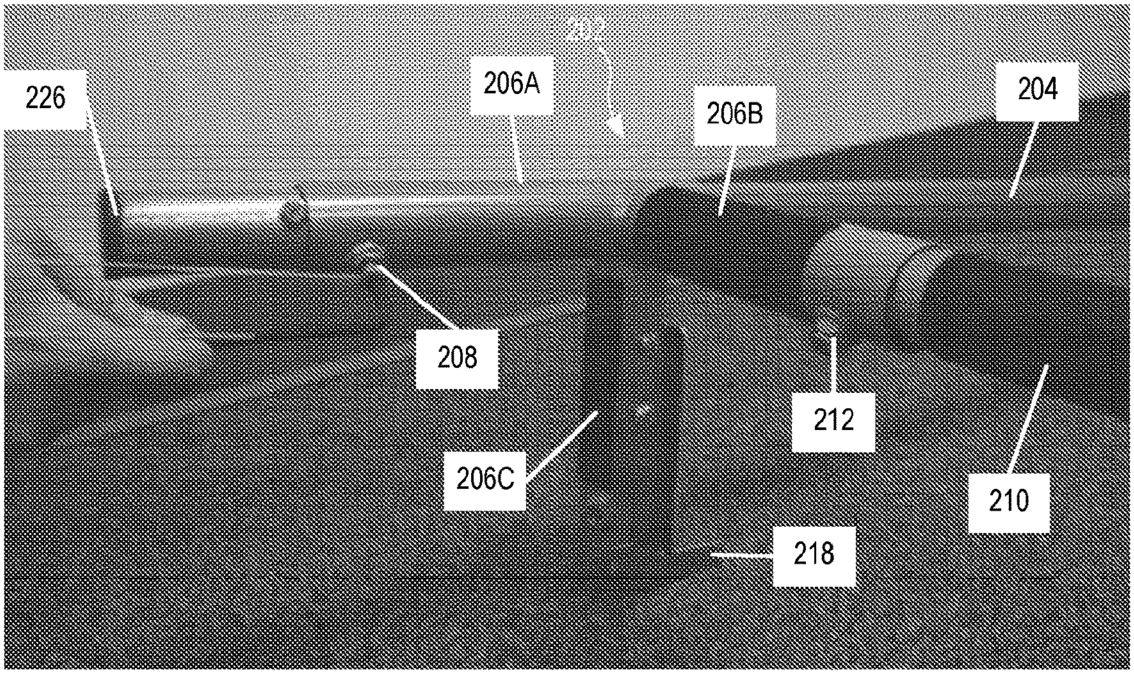
FIG. 3 depicts a more detailed view of a corner bracket of the frame of FIG. 2, in embodiments.

FIG. 2 depicts frame 116 without enclosure 101 in more detail. In embodiments, frame 116 may be assembled from a combination of straight poles, curved poles and brackets. Although a specific embodiment is described herein, it should be understood that other combinations of straight and/or curved poles are contemplated. FIG. 3 is a more detailed view of a corner bracket of frame 116. The portion of frame 116 shown in FIG. 3 is rotated 90 degrees from the orientation of frame 116 in FIG. 2. FIGS. 2 and 3 are best viewed together in the following description. Components described separately may be combined into a single component and single components may be split into two or more components without departing from the embodiments discussed herein.

In general, bottom corner brackets 202 receive bottom end poles 210 and bottom side poles 214 to form a base of frame 116. Each corner bracket 202 includes three tubes meeting at right angles to form a bottom corner of frame 116. Tube 206A receives vertical corner pole 204, which passes all the way through tube 206A to form a foot 226 of frame 116 that rests on the floor. It may be secured in place with hex screw 208, for example, although other components for securing frame elements are contemplated. Further, a number of securing components greater or less than those shown may be used. Tube 206B receives bottom end pole 210, which may be secured with hex screw 212. Tube 206C receives bottom side pole 214. In embodiments, bottom side pole 214 may be in two halves joined by bottom connector 216 and secured by hex screws. Further, more or less than two bottom side poles 214 may be used to provide the preferred length for a safety bed 100. Tube 206C also includes a tab 218, which will be discussed in more detail below. Lengths of hook-and-loop tape may be secured to various places on frame 116, such as tube 206C and bottom side pole 214, for attaching enclosure 101 to frame 116. Corner brackets 202, bottom end poles 210 and bottom side poles 214 form a base frame.

Vertical corner poles 204 extend upward from their associated corner bracket 202 and are each attached to top corner connector 220 at an upper end. As described above for the base frame, an upper frame is formed by top corner connectors 220, top end poles 222 and top arch poles 224. In embodiments, two top arch poles 224 are joined by top connector 228, however, more or less than two top arch poles 224 may be used to provide a preferred length for safety bed 100. In embodiments, frame 116 may be made of metal but any material capable of supporting a user's weight and enclosure 101 may be used.

Figure 4:
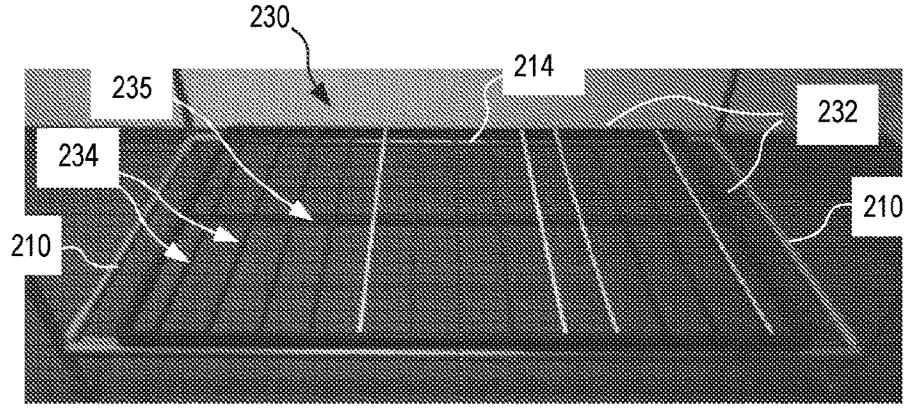
FIG. 4 depicts a mattress support structure for use with the safety bed of FIG. 1, in embodiments.
Figure 5:
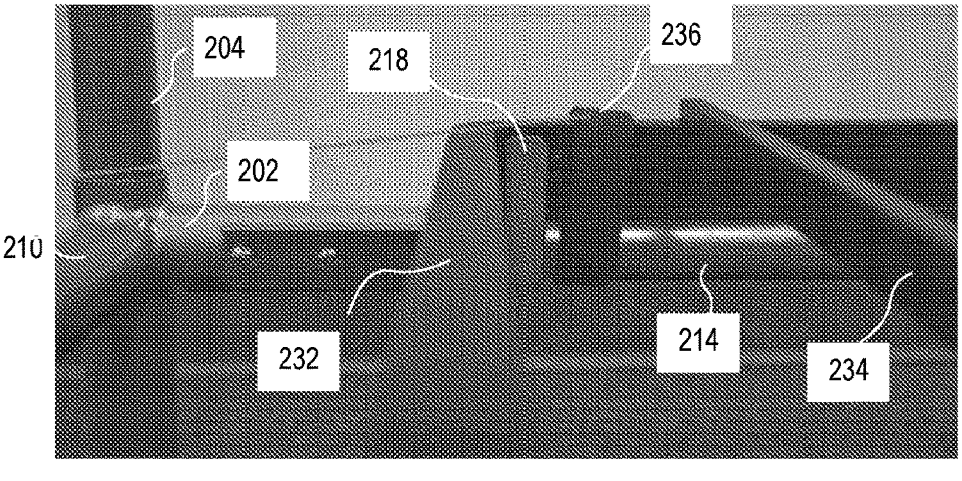
FIG. 5 depicts a more detailed view of the frame of FIG. 2 and the mattress support structure of FIG. 4, in embodiments.

As shown in FIGS. 4 and 5, a mattress support structure 230 rests on bottom side poles 214 and/or bottom end poles 210. Mattress support structure 230 may include a frame 232 spanned by a plurality of slats 234 and a cross brace 235. The slats and cross brace shown in FIG. 4 are for purposes of illustration only and any number may be used as long as it is sufficient to support a mattress and a user of safety bed 100. Although an embodiment of a mattress support structure is shown, embodiments herein are not limited to this specific structure. As shown in FIG. 5, tab 218 on tube 206C at each corner engages with each corner of mattress support structure 230 to retain it securely in place on bottom side poles 214. A hook-and-loop strap 236 may be used in addition to or instead of tab 218 to secure mattress support structure 230 to bottom side poles 214. Mattress support structure 230 may be positioned in several locations on the base of frame 116 without departing from embodiments disclosed herein.

Figure 6:
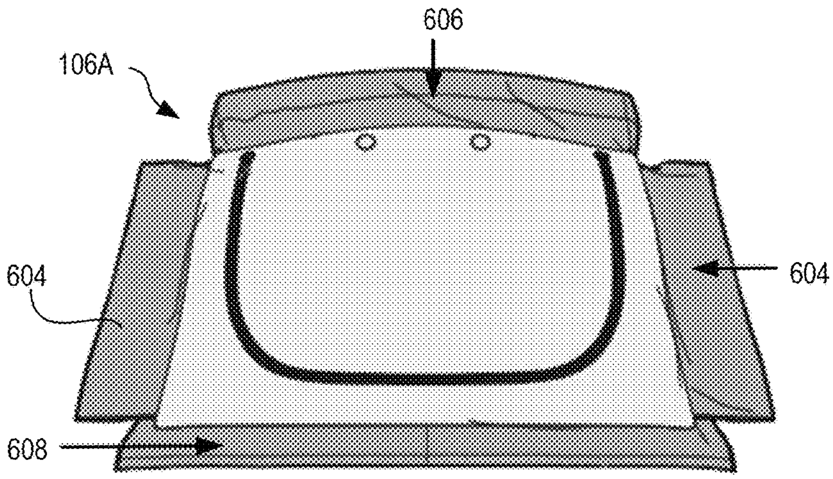
FIG. 6 depicts a detailed view of a side wall of an enclosure for the safety bed of FIG. 1, in embodiments.
Figure 7:
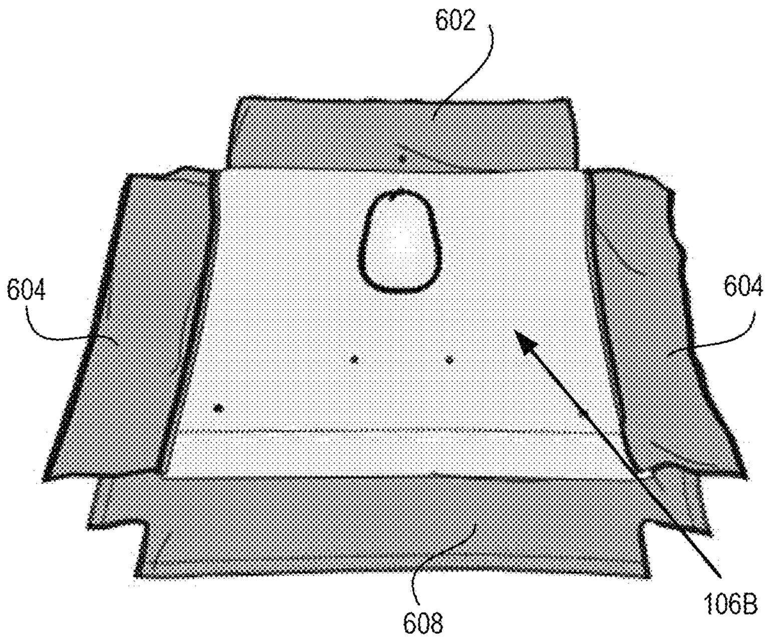
FIG. 7 depicts a detailed view of a head wall of an enclosure for the safety bed of FIG. 1, in embodiments.
Figure 8:
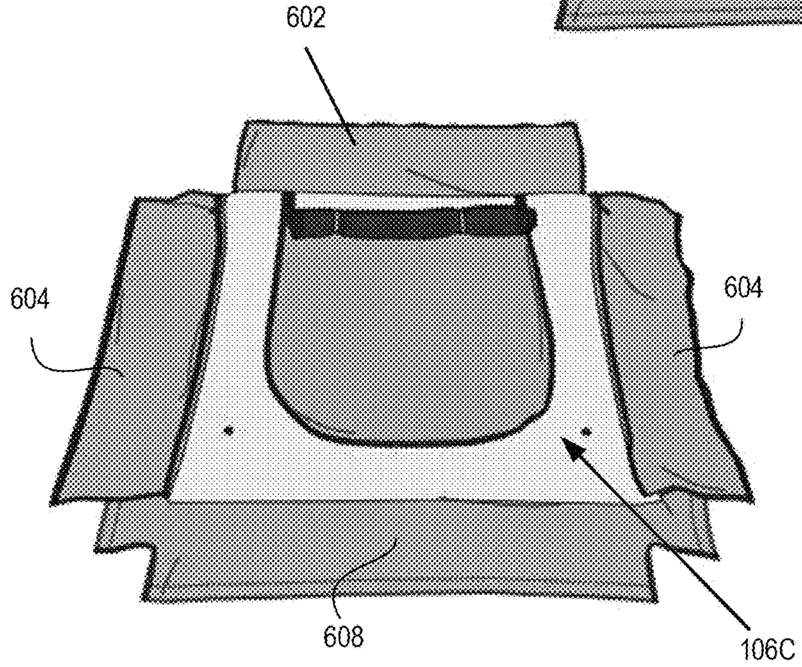
FIG. 8 depicts a detailed view of an end wall of an enclosure for the safety bed of FIG. 1, in embodiments.
Figure 9:
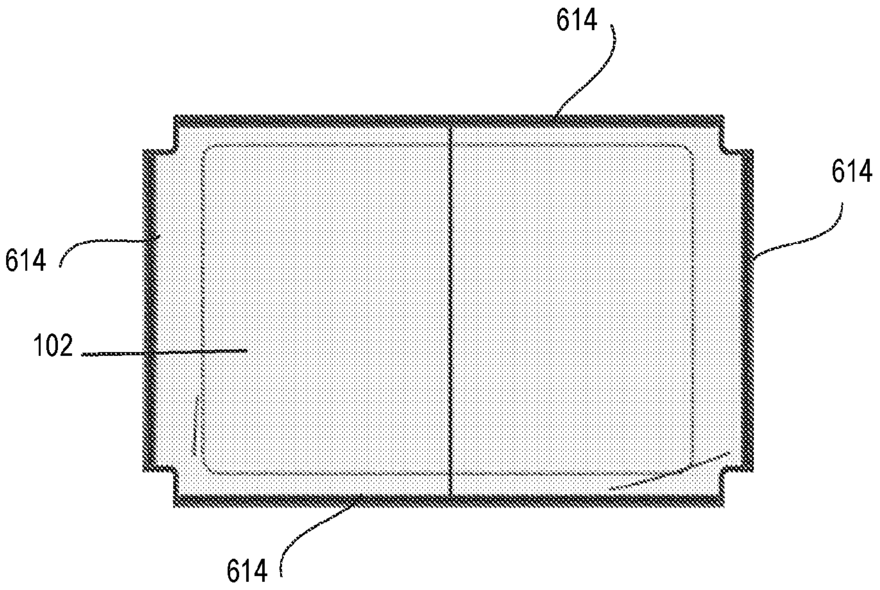
FIG. 9 depicts a detailed view of a base of an enclosure for the safety bed of FIG. 1, in embodiments.
Figure 10:
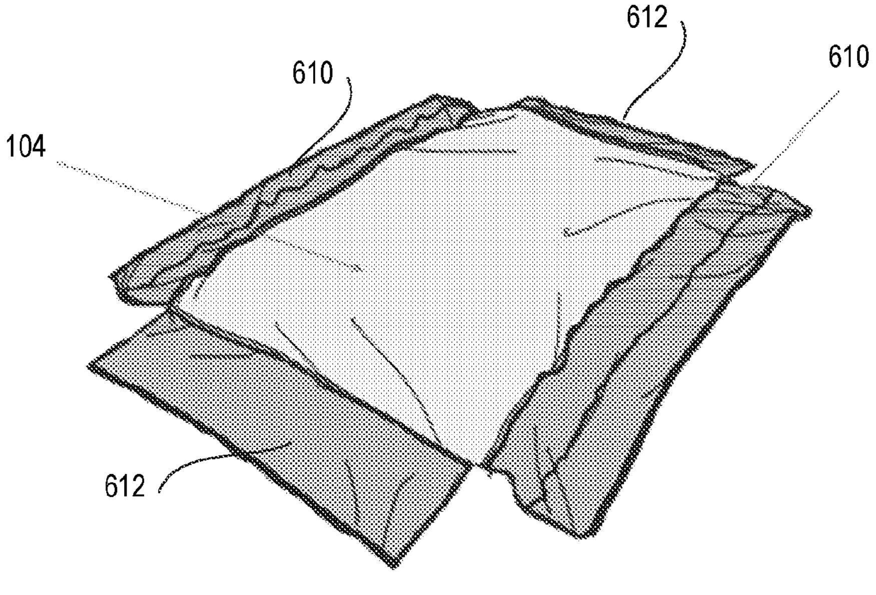
FIG. 10 depicts a detailed view of a ceiling of an enclosure for the safety bed of FIG. 1, in embodiments.

FIGS. 6-10 show detailed views of various sections of enclosure 101 prior to assembly. FIG. 6 shows side wall 106A of FIG. 1. FIG. 7 shows head wall 106B. FIG. 8 shows end wall 106C. FIG. 9 shows base 102 and FIG. 10 shows ceiling 104. Together the walls 106, base 102 and ceiling 104 of FIGS. 6-10 are assembled to form enclosure 101. Various techniques may be used to assemble enclosure 101, including sewing and fusing, for example. Edges of components may be finished in various ways to provide durability or comfort. In embodiments, components described separately herein may be combined, for example, a side wall 106A and end wall 106C may be formed from one length of material. Each of walls 106, base 102 and ceiling 104 are generally rectangular.

Extensions 602, 604, 606, 608, 610 and 612 are incorporated around the edges of walls 106, base 102 and ceiling 104 are used to from loops that will secure enclosure 101 to frame 116. For example, extensions 606 on side walls 106A may be attached to extensions 610 on ceiling 104 in such a way as to form a loop through which arch poles 224 pass. In embodiments, any of the loops discussed herein may be formed as a solid piece or as two separable pieces that are secured to each other using a zipper or hook-and-loop tape. Extensions 602 on head wall 106B and end wall 106C may be attached to extensions 612 on ceiling 104. Extensions 604 on adjoining edges of side walls 106A and head wall 106B or end wall 106C may be attached to each other. Extensions 608 on the bottom of all walls 106* may be secured to side edges 614 of base 102 to form a loop. In embodiments, walls 106 may be attached to base 102 with a seam and side edges 614 may be used to wrap around bottom end poles 210 and bottom side poles 214.

Enclosure 101 may be made from a durable canvas fabric such as Sunbrella®. A mesh fabric may be used for portions of enclosure 101 such as openings 108. The fabric used for enclosure 101 may be treated for water and stain resistance. In embodiments, enclosure 101 may be made from a thicker fabric or foam material that absorbs sound.

Figure 11:
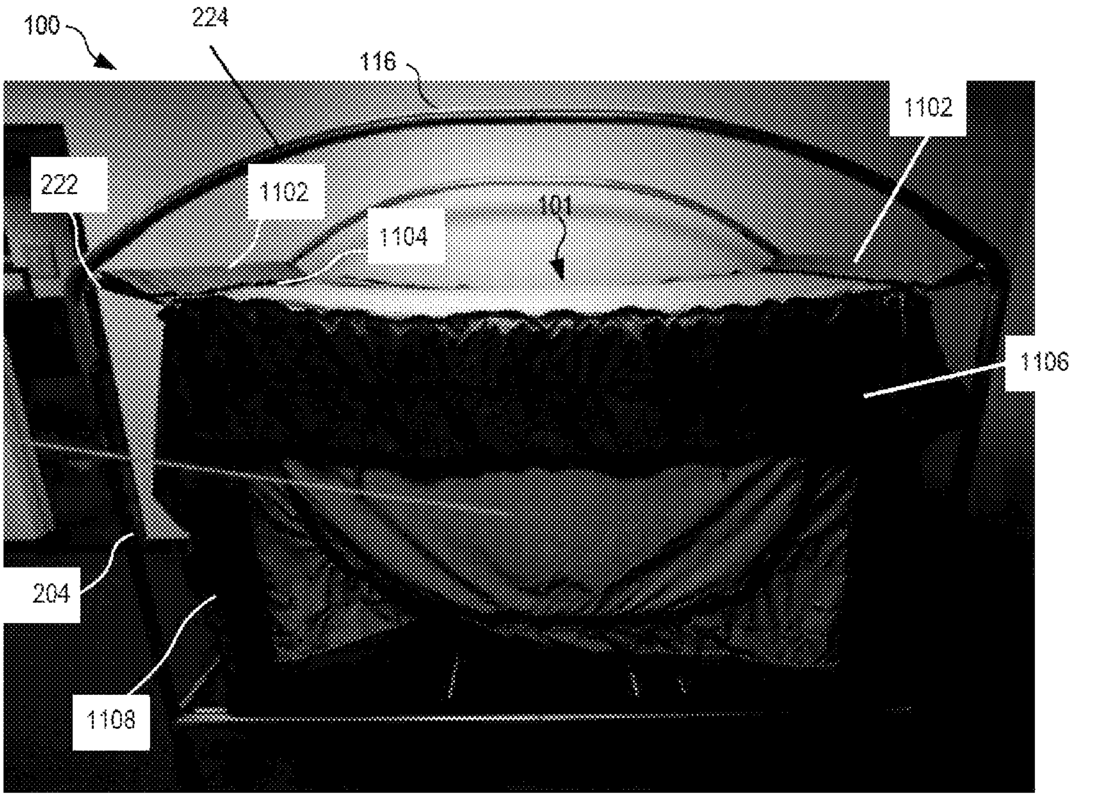
FIG. 11 depicts an intermediate step in attaching an enclosure to the frame of FIG. 2, in embodiments.

FIG. 11 depicts enclosure 101 at an intermediate step of attachment to frame 116. End loops 1102 are wrapped around top end poles 222 and secured with zipper 1104. Loops 1106 formed from extensions 606 and 610 may be attached to top arch poles 224 with a zipper in the same way. Extensions 1108 formed from extensions 604 may be used to attach side corners of enclosure 101 to the four vertical corner poles 204. Hook-and-loop loop is used to attach base 102 to frame 116.

Figure 12:
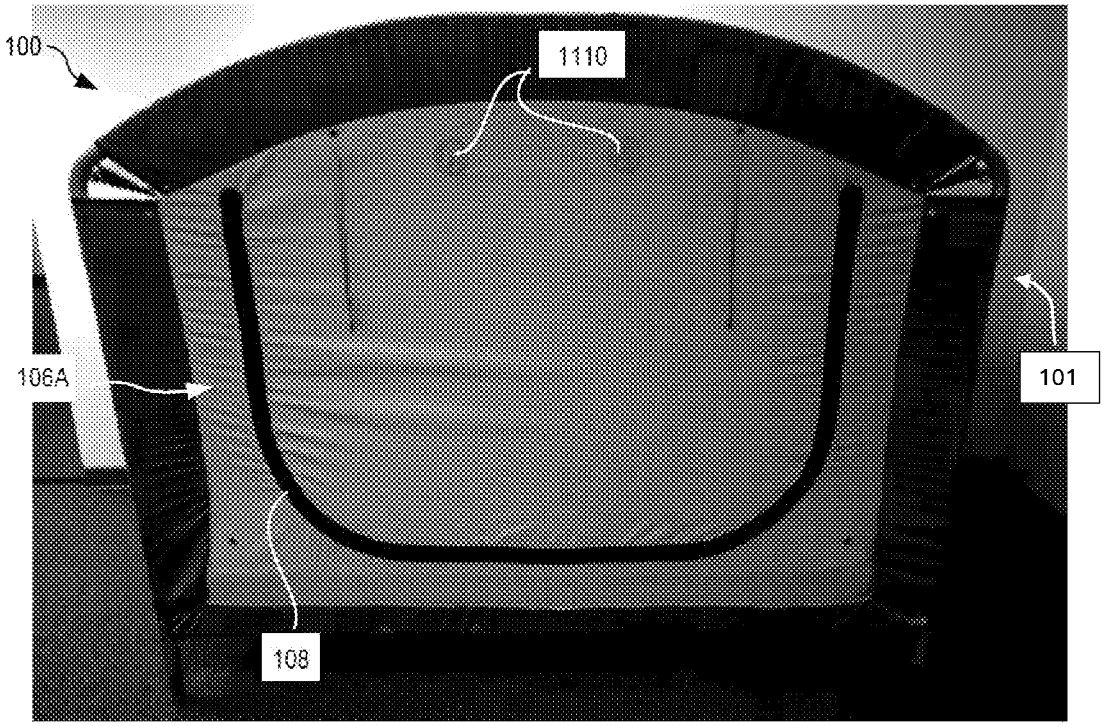
FIG. 12 depicts a side view of an enclosure completely attached to the frame of FIG. 2, in embodiments.

FIG. 12 depicts safety bed 100 with enclosure 101 fully attached to frame 116. Although various attachment mechanisms are shown, others are contemplated. Enclosure 101 may be attached to frame 116 using hook-and-loop tape or snaps, for example. In embodiments, decorative features may be added to safety bed 100 to increase the appeal of safety bed 100 to children. For example, appliques or other techniques may be used to represent eyes 1110 while opening 108 of side wall 106A represents a mouth. Although an arrangement of decorative features is shown herein, safety bed 100 is not limited to any particular color or design. Decorative features may be incorporated into enclosure 101 or attached with hood-and-loop tape, snaps, or any convenient attachment method.

In embodiments, frame 116 may be adjusted to ensure proper tension of enclosure 101. For example, frame 116 may be expanded using hex screws as described above to accommodate stretching of enclosure 101 so that proper tension of base 102, ceiling 104 and side walls 106 may be maintained. The use of hook-and-loop tape on various areas of frame 116 to attach portions of enclosure 101 allows frame poles to be rotated to tighten enclosure 101.

In embodiments, safety bed 100 as disclosed herein may include several features that increase safety and comfort of those using the bed. In embodiments, features may be added or removed at any time. For example, varying levels of padding may be provided in walls 106A, 106B and 106C, whether through the thickness of a single material or extra padding layers. Any thickness of padding in walls 106* as well as ceiling 104 and base 102. This provides an environment wherein an occupant of the bed is protected from injuring themselves during a seizure, for example.

Figure 13:
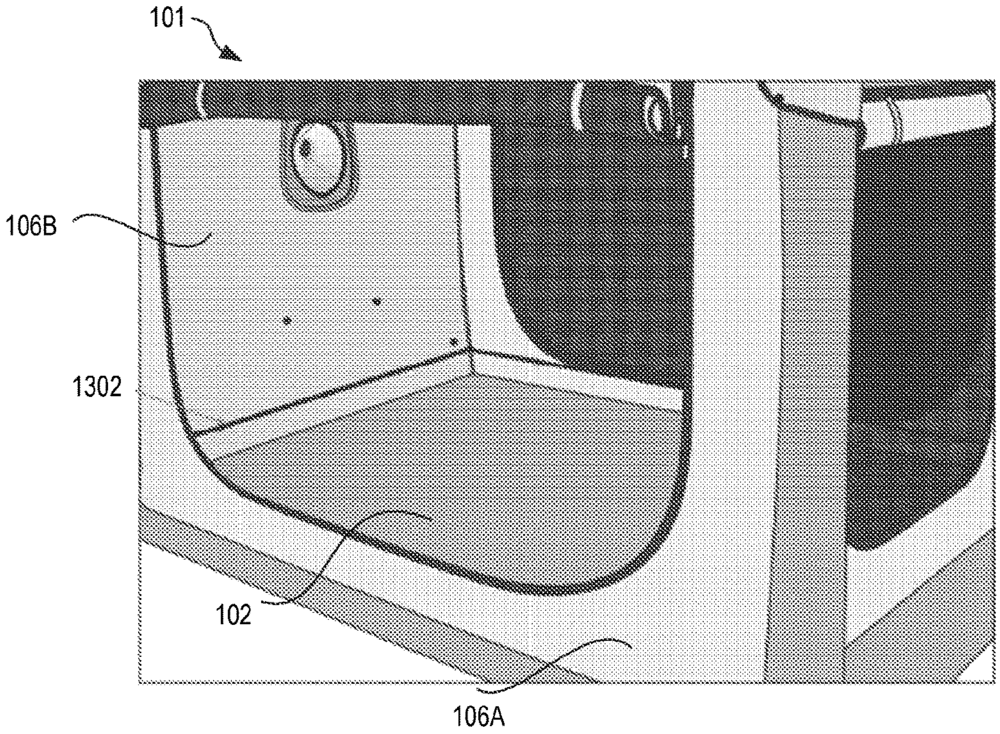
FIG. 13 depicts an inside view of an enclosure for the safety bed of FIG. 1, in embodiments.

Embodiments of safety bed 100 may include a mechanism for attaching a sheet directly to enclosure 101. FIG. 13 depicts an inside view of enclosure 101. First half 1302 of a zipper attachment may be provided at a location on the walls of enclosure such that it will be at approximately the same height as the top of a mattress (not shown) placed in enclosure 101. In embodiments, a mattress used with safety bed 100 is a full-size mattress having a height less than approximately 10 inches. Depending on the height of the mattress, first half 1302 of the zipper may be at, slightly above or slightly below the top of the mattress. In embodiments, first half 1302 of the zipper extends around the entire circumference of enclosure 101, but other arrangements are contemplated, for example, each wall 106* may include a separate section of a zipper.

Figure 14:
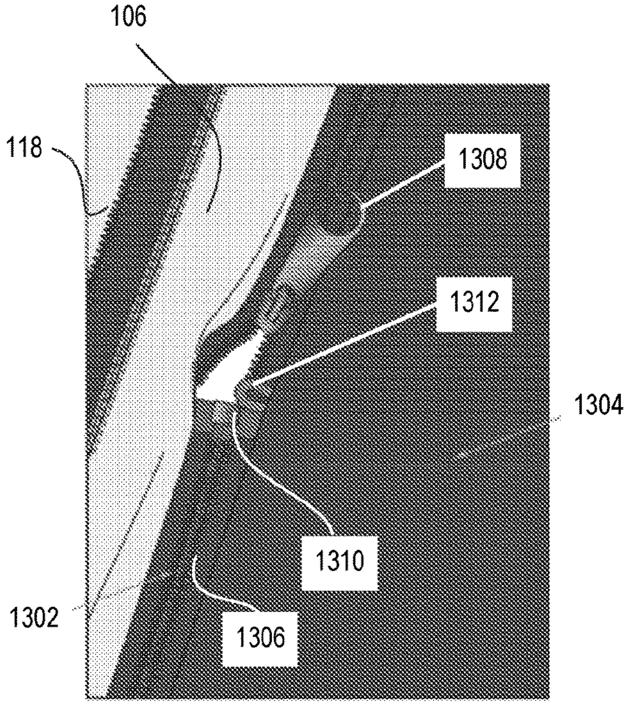
FIG. 14 depicts more detailed view of a zipper pull for attaching a sheet to the inside of the enclosure of FIG. 13, in embodiments.
Figure 15:
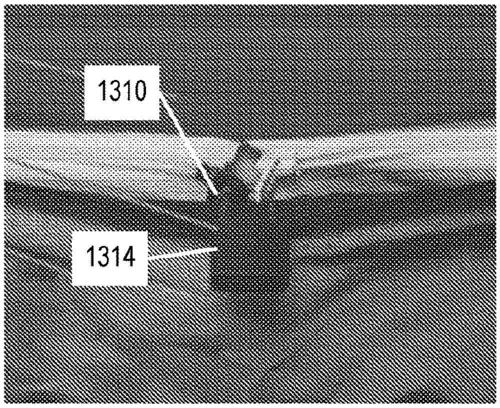
FIG. 15 depicts another view of locking the zipper pull of FIG. 14.

FIGS. 14 and 15 depict attachment of a sheet 1304 to the inside of enclosure 101. A connecting half 1306 of zipper is formed around the circumference of sheet 1304 for attachment to first half 1302. Sheet 1304 is attached to enclosure 101 after a mattress is placed in enclosure 101. Zipper pull 1308 is pulled around the circumference of sheet 1304 to meet zipper stop 1310. For ease of use, zipper stop 1310 is positioned close to one of openings 108 in enclosure 101. In embodiments, a loop 1312 may be provided near zipper stop 1310 so zipper pull 1308 may be retained in place by lock 1314 through both loop 1312 and a hole in the end of zipper pull 1308 as shown in FIG. 15.

Figure 16:
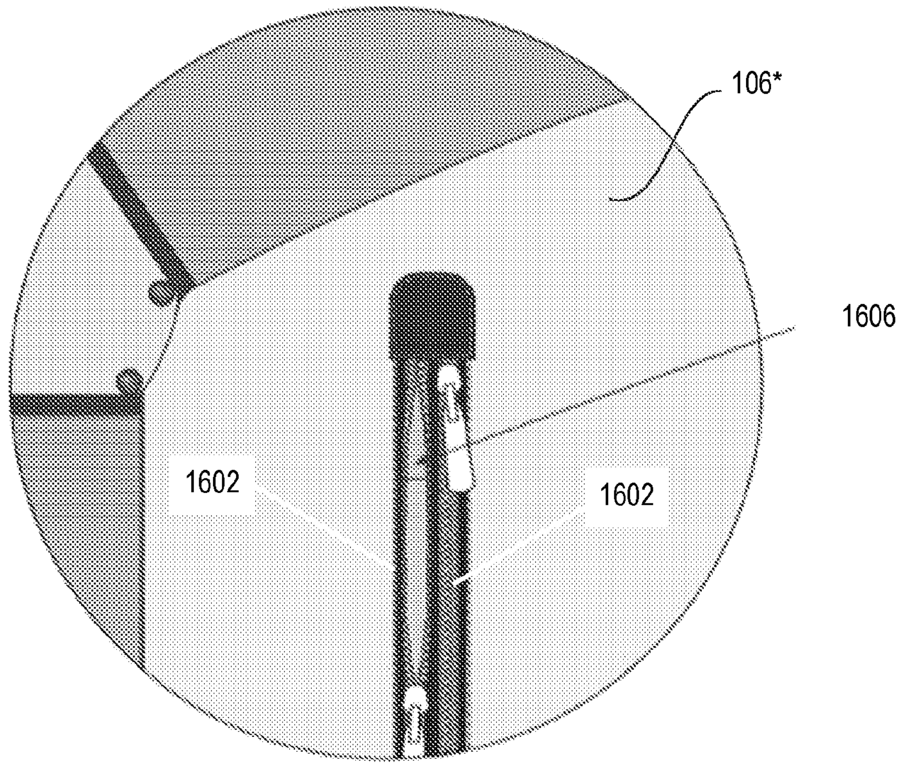
FIG. 16 depicts a zipper safety pocket from the outside of the safety bed of FIG. 1, in embodiments.
Figure 17:
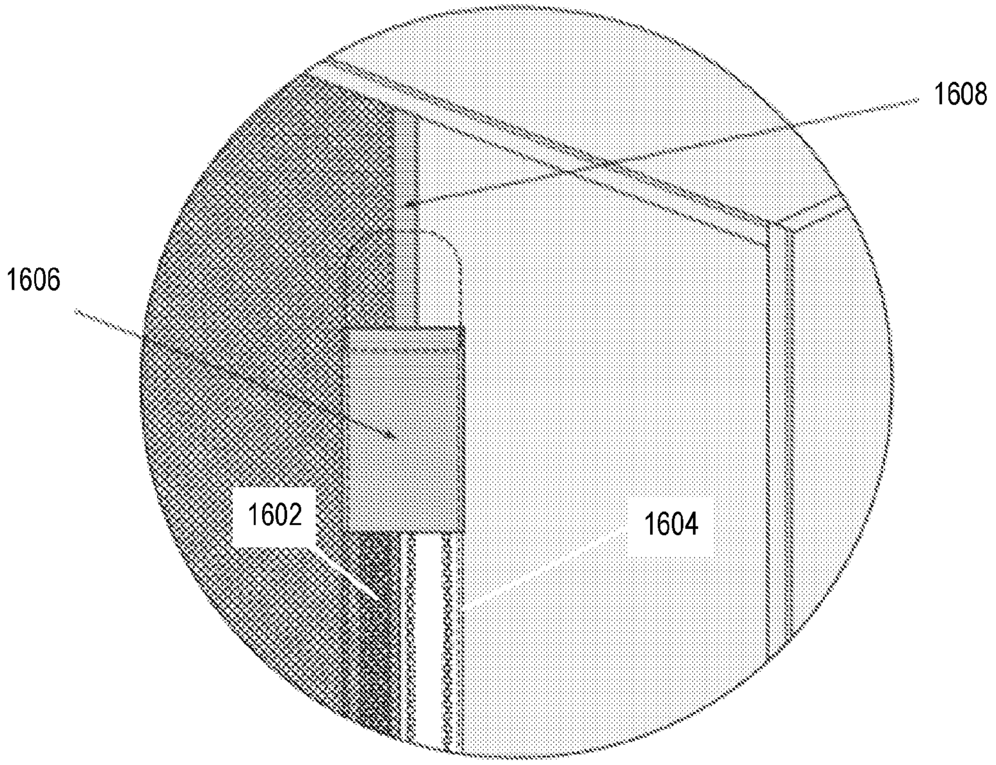
FIG. 17 depicts a zipper safety pocket from the inside of the safety bed of FIG. 1, in embodiments.

Another feature is shown in FIGS. 16 and 17. Flaps 110 may be opened and closed by means of double zipper arrangement. A first zipper 1602 may be used to secure a mesh flap over opening 108. In addition, an opaque fabric flap may be closed over opening 108 using second zipper 1604. FIG. 16 shows an outside view one end of first zipper 1602 and second zipper 1604 in enclosure 101. FIG. 17 shows an inside view. Zipper safety pocket 1606 is provided on the inside of enclosure 101 to prevent manipulation of zippers 1602 and 1604 from inside enclosure 101. Safety pocket 1606 may be placed on either or both ends of zippers 1602 and 1604. Seams on the inside of enclosure 101 may be finished with seam tape, in embodiments.

Figure 18:
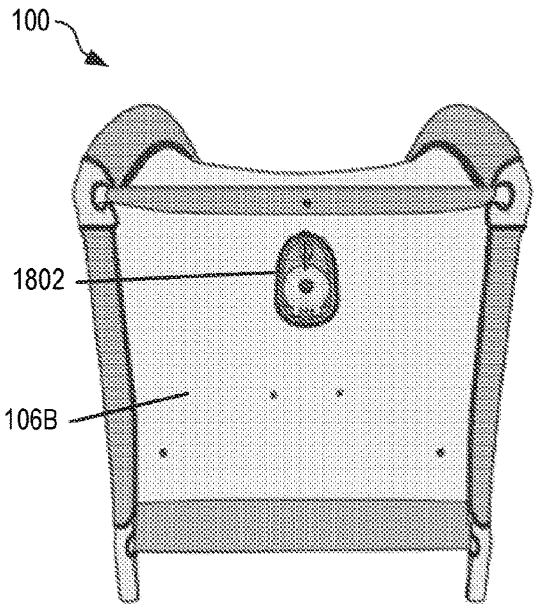
FIG. 18 depicts an end wall of the safety bed of FIG. 1 with an installed electronics hub, in embodiments.
Figure 19:
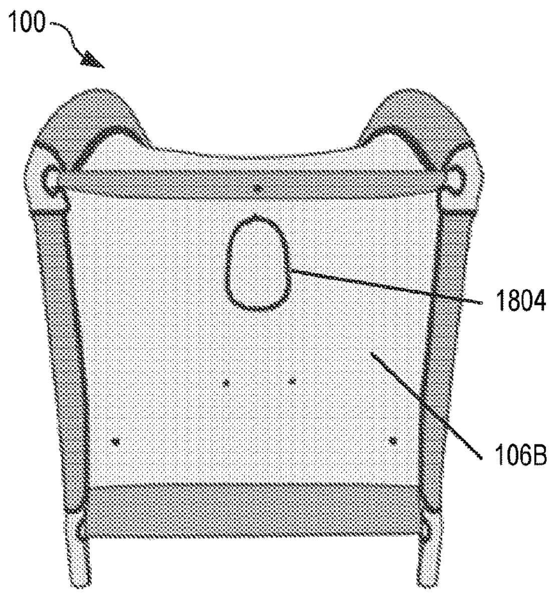
FIG. 19 depicts an end wall of the safety bed of FIG. 1 with a fabric cover installed in place of the electronics hub of FIG. 18, in embodiments.

Other features of safety bed 100 are described in connection with FIGS. 18-20, which are best view together in the following description. In embodiments, an electronics hub 1802 may be attached to an opening in head wall 106B as shown in FIG. 18. In embodiments, electronics hub 1802 may also be attached to any surface in enclosure 101. In an embodiment, electronics hub 1802 is attached with a zipper. Alternatively, a fabric cover 1804 may be zipped into the opening in head wall 106B as shown in FIG. 19 when safety bed 100 is used without electronics hub 1802. Other mechanisms of attaching electronics hub 1802 are also contemplated within the scope of this disclosure. In embodiments, head wall 106B may include a safety barrier (not shown) between electronics hub 1802 and the interior of safety bed 100. For example, a tensioned mesh screen, fabric and/or padding may be provided to protect both electronics hub 1802 and an occupant of safety bed 100.

Figure 20:
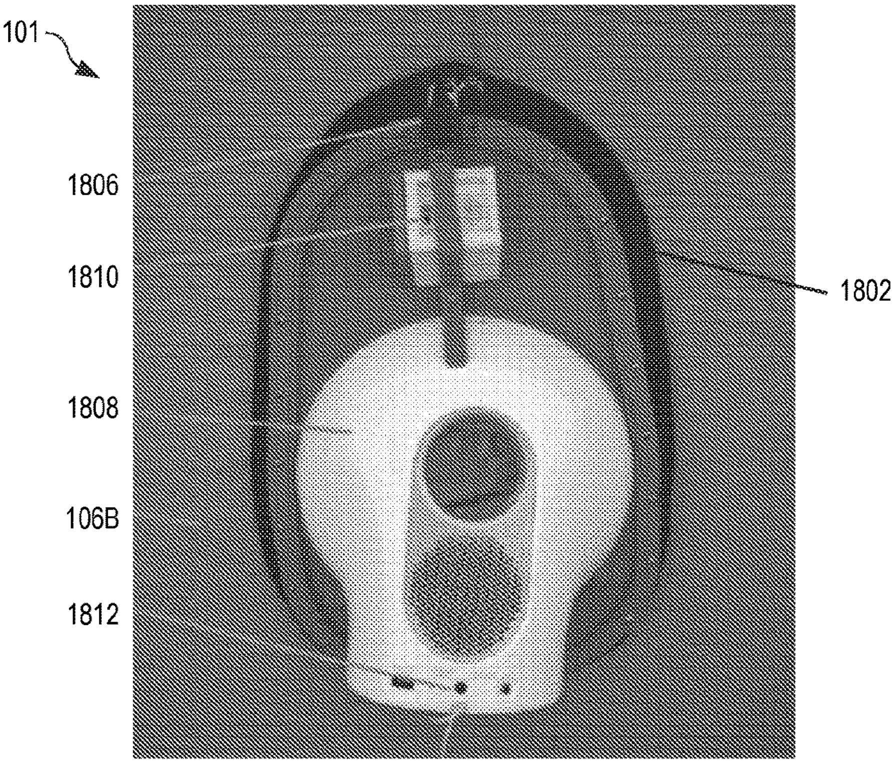
FIG. 20 depicts a more detailed view of the electronics hub of FIG. 18, in embodiments.

FIG. 20 is a close-up view of an embodiment of electronics hub 1802 as seen from the exterior of enclosure 101. Although various features are described herein, other features and a different physical arrangement of those features are contemplated within the scope of this disclosure. In an embodiment, electronics hub 1802 is attached with a zipper, which may be locked in place using lock 1806. Features included in electronics hub 1802 may be connected to a network and controlled from a remote device, such as a mobile phone. A variety of components of electronics hub 1802 are described herein, however, it is not limited to the specific set of components described. Electronics hub 1802 is modular and individual components may be added or replaced with a filler piece as desired.

Sensory hub 1808 allows several features of safety bed 100 to be controlled remotely. A light may be controlled to customize the color, brightness, and timing to improve circadian rhythm or create a subtle alarm. It may also be controlled to change gradually over time and act as a sunrise in the morning, sunset at night. The light may also be used for meditative breathing with a light pulsing operation. Sensory hub 1808 may include speakers for controlling the audio environment with music, white noise, audiobooks, or nature sounds. A mattress vibration pad may be attached to sensory hub 1808 to provide soothing tactile stimulation to help with anxiety & vestibular processing. In embodiments, an aromatherapy dispensing device may be included in sensory hub 1808 or as a separate feature to provide soothing olfactory inputs with lavender, vanilla and other scents.

Electronics hub 1802 also includes a camera and microphone 1810 which may be remotely controlled and monitored. Camera and microphone 1810 may provide a live view of the inside of enclosure 101 from anywhere via a mobile device, for example. Camera and microphone 1810 may also be used to communicate remotely and provide video footage to therapists & doctors. Camera and microphone 1810 may include night vision and local/cloud recording of data.

Other features which may be included in electronics hub 1802 include motion and sound based sensors which generate alerts if the user leaves their bed, room, or house or has incontinence issues or seizures. A notification may be provided to a caregiver's device and can also sound an alarm if needed. In embodiments, environmental sensors showing temperature, humidity, and sound levels inside the canopy are included in electronics hub 1802 to better adjust the environment for sleep and relaxation. A power cord 1812 may be plugged into a power source. Electronics hub 1802 may be integrated with smart home devices such as Alexa and Google Home.

Figure 21:
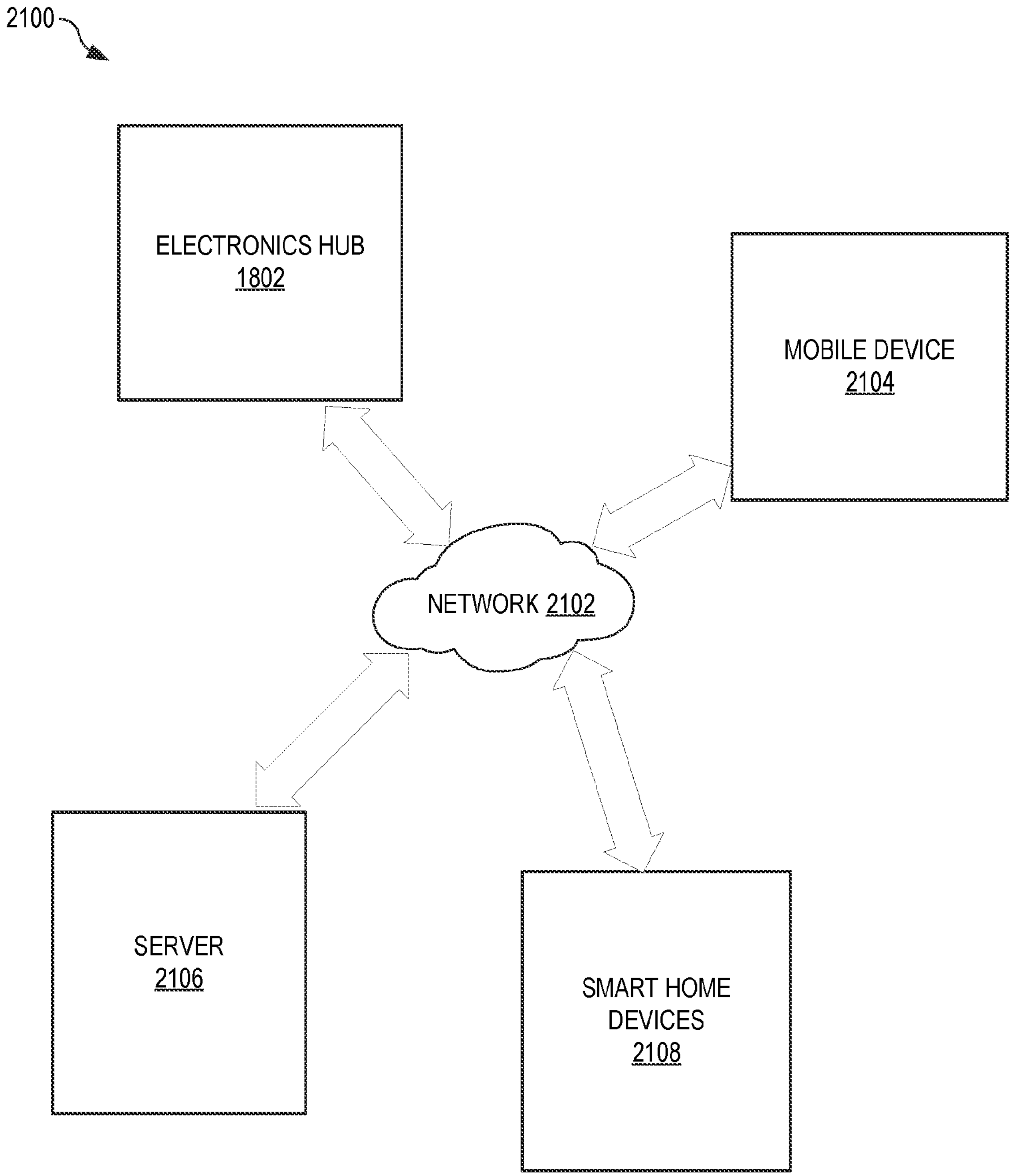
FIG. 21 is a block diagram of computing elements that may be used to control the electronics hub of FIG. 18, in embodiments.

FIG. 21 is a block diagram of computing elements 2100 that may be used to interact with electronics hub 1802. A network 2102 may represent a Wi-Fi, LAN, WAN or cellular network, for example. Electronics hub 1802 may include a communications interface such as one or more wireless antennas for communicating with other devices over network 2102. In embodiments, electronics hub 1802 may be connected to a router in a user's home with a wireless or wired connection. A mobile device 2104 such as a smartphone or tablet may communicate with electronics hub 1802 over network 2102. Mobile device 2104 may also communicate with electronics hub 1802 using a Bluetooth® connection. Other devices may communicate with electronics hub 1802 to provide the functions discussed herein, such as server 2106 or smart home devices 2108. Server 2106 may represent any computers or software that provide the functions disclosed herein, including remote monitoring by a doctor or other healthcare professional, for example.

Additional features may be incorporated into enclosure 101 as described above for electronics hub 1802. For example, a fan may be included to improve ventilation. A video screen may be included to provide visual interaction, such as with a caregiver or doctor, or to enable entertainment or relaxation. An integrated projection may be used to display visuals on ceiling 104 and/or walls 106.

A safety bed for children and adults with special needs has been disclosed herein. Various features have been described but a representative safety bed is not limited to any specific set of features. Features of safety bed 100 include a tensioned enclosure, a zippered safety sheet, sensory features within the bed, remote monitoring integrated into the bed, and sensors to detect conditions and alert caregivers to impending circumstances of a user of the bed.

Enclosure 101 creates a sensory cocoon and cleanable safety zone to prevent elopement, injury, & entrapment. Enclosure 101 is tensioned across the steel frame to provide 360 degrees of tensioned padding with space between walls and all hard points (poles, walls, other furniture, etc). Safety sheets zip to the sidewall above the mattress to prevent entrapment and burrowing. A camera and microphone allows a live view from anywhere via phone, including communicating remotely and providing video footage to therapists & doctors. Motion and sound based alerts indicate if the user leaves their bed, room, or house or has incontinence issues or seizures. Triggers notification may be sent to a caregiver's phone and can also sound an alarm if needed. Environmental sensors show temperature, humidity, and sound levels inside the canopy to better adjust the environment for sleep and relaxation. Other sensors may detect smoke and carbon monoxide.

Lights inside enclosure 101 may be customized to adjust the color, brightness, and timing to improve circadian rhythm or create a subtle alarm. They may also act as a sunrise in the morning, sunset at night or be used for meditative breathing with light pulsing. Speakers may control the audio environment within enclosure 101 with music, white noise, audiobooks, or nature sounds. Mattress vibration may provide soothing tactile stimulation to help with anxiety & vestibular processing. Aromatherapy may provide soothing olfactory inputs with lavender, vanilla and other scents.

In embodiments, safety bed 100 may provide an automated environment by using machine learning and predictive analytics to correlate changes in environment, medication, diet, or therapy with changes in physiological outputs such as heart rate, breathing rate, quality of sleep, etc. In embodiments, safety bed 100 may be programmed to automatically perform a calming sensory routine if it has detected a disturbance or wakefulness in the user as well as collect data from the bed that enables doctors and therapists to do remote coaching to improve sleep and behavior. For example, camera and/or microphone 1810 as well as other sensors may be used detect movement or agitation of an occupant of safety bed 100. Machine learning and predictive analytics based on an individual user's history and/or a composite history of all users may be correlated to the detected movement or agitation for activating any or all of the features described herein. An automatic calming sensory routine may be performed.

Likewise, sensors may collect data on movement in general, or specific types of behavior such as a seizure or epileptic activity. Sensors may also detect incontinence issues such as urine, feces or vomit. Sensors and/or video analysis may be used to enable monitoring of the breathing activity of an occupant of safety bed 100, as well as air quality such as carbon dioxide or pollen. Sensors may also be used to detect conditions that may lead to a pressure sore and generate an alert in response. The data may be shared with a healthcare professional in real time or at a later time for diagnosis and treatment recommendations.

Any of the components described herein may be integrated with other health systems or electronic health record (EHR) systems to enable remote monitoring of an occupant of safety bed 100 and telehealth capabilities. Data accumulated over time may be analyzed to provide suggestions on improving the environment, timing and other aspects of safety bed 100 to optimize the occupant's experience. Further, sensory packages may be developed that draw on a media library of sounds, light, visuals and any combination thereof to provide customized experiences of safety bed 100 that may be selected and controlled using an application on a mobile or other computing device.

Changes may be made in the above methods and systems without departing from the scope hereof. It should thus be noted that the matter contained in the above description or shown in the accompanying drawings should be interpreted as illustrative and not in a limiting sense. Herein, and unless otherwise indicated: (a) the adjective "exemplary" means serving as an example, instance, or illustration, and (b) the phrase "in embodiments" is equivalent to the phrase "in certain embodiments," and does not refer to all embodiments. The following claims are intended to cover all generic and specific features described herein, as well as all statements of the scope of the present method and system, which, as a matter of language, might be said to fall therebetween.

What is claimed is:

1. A safety bed, comprising:

a frame, said frame comprising:

a base frame having four corner brackets, each corner bracket receiving one end of a side pole and an end pole, the side and end poles having hook-and-loop tape secured along their length;

four vertical poles, a lower end of each vertical pole received in a respective one of the four corner brackets;

four top corner connectors attached to an upper end of a respective vertical pole;

two top end poles connected between top corner connectors parallel to the end poles of the base frame; and arch poles connected between top corner connectors parallel to the side poles of the base frame;

a mattress support structure supported by the base frame;

an enclosure attached to the frame, said enclosure comprising:

a ceiling, a base and four walls, wherein the four walls are secured to each other at vertical sides and the ceiling and base are secured to the four walls at a top and bottom, respectively, of the four walls to form the enclosure;

a plurality of extensions incorporated at each of top and side edges of the enclosure, for securing the enclosure to the frame; and bottom extensions incorporated at the bottom of the four walls, the bottom extensions including hook-and-loop tape for connecting to the hook-and-loop tape on the side and end poles of the base frame; and one or more sensors for monitoring a condition within the enclosure; and one or more devices for providing a stimulus to an occupant of the safety bed.

2. The safety bed of claim 1, further comprising a mattress within the enclosure and supported by the mattress support structure.

3. The safety bed of claim 2, further comprising a sheet attached to the four walls of the enclosure at a position approximately equal to a top of the mattress.

4. The safety bed of claim 2, wherein the one or more devices further comprise a vibration pad for causing the mattress to vibrate.

5. The safety bed of claim 1, wherein the four walls further comprising two side walls, a head wall and an end wall.

6. The safety bed of claim 5, wherein the two side walls and the end wall further comprise a zippered opening.

7. The safety bed of claim 1, wherein at least one of the one or more sensors and the one or more devices are included in an electronics hub attached to a wall of the enclosure adjacent to the ceiling with a zipper.

8. The safety bed of claim 7, wherein the electronics hub further comprises a communications interface for connecting to a communications network so that the electronics hub may be controlled or monitored remotely.

9. The safety bed of claim 1, wherein the one or more devices further comprise a speaker connected to a computing device over a network.

10. The safety bed of claim 1, wherein the one or more devices further comprise an aromatherapy dispensing device.

11. The safety bed of claim 1, wherein the one or more sensors further comprise sensors for detecting movement or sound of an occupant of the safety bed.

12. The safety bed of claim 1, wherein the one or more sensors further comprise environmental sensors for detecting temperature or humidity levels inside the enclosure.

13. The safety bed of claim 1, wherein the enclosure further comprises padding.

14. The safety bed of claim 1, wherein the one or more devices further comprise a light source connected to a computing device over a network.

15. The safety bed of claim 1, wherein the one or more sensors further comprise a camera and a microphone.

16. The safety bed of claim 3, wherein the sheet is attached to the four walls of the enclosure by a first half of a zipper provided at a location on the walls of the enclosure at approximately the same height as the top of a mattress placed on the mattress support structure, and a connecting half of the zipper is formed around the circumference of sheet for attachment to the first half.

17. The safety bed of claim 16, further comprising a zipper stop;

a loop secured to the enclosure adjacent to the zipper stop; and a lock configured to secure a zipper pull through the lock.

* * * * *